United States Patent [19]

Yabrov

[11] Patent Number: 4,480,032

[45] Date of Patent: Oct. 30, 1984

[54] NATURAL MIXTURE OF TYPE I AND TYPE II INTERFERONS

[76] Inventor: Alexander A. Yabrov, 45 Wiggins St., Princeton, N.J. 08540

[21] Appl. No.: 206,401

[22] Filed: Nov. 13, 1980

[51] Int. Cl.³ ..................... C12P 21/00; A61K 45/02; C07G 7/00

[52] U.S. Cl. ..................... 435/68; 424/85; 260/112 R

[58] Field of Search ..................... 424/85; 260/112 R; 435/68, 811

[56] References Cited

PUBLICATIONS

Paucker, K., Texas Reports on Biology and Medicine, vol. 35, pp. 23–28, 1977.
Torma and Paucker, J. Biol. Chem., vol. 254, pp. 4810–4816, 1976.
Chadha, K. et al., Biochemistry, vol. 17, 196–200, 1978.
Morgensen, K., Pharm. Ther. H., vol. 1, pp. 369–381, 1977.
Biology of the Lymphokines, Epstein, Lois B., Academic Press, Inc., 1979, pp. 445–447; 453–454.
Osborne, L., Cellular Immunology, vol. 53, p. 65, 1980.
Induction of Interferon in Human Lymphoblastoid Cells by Sendai and Measles Viruses, Volckaert et al., Dept. of Chem., Biol & Microb; Limburgs Universitair Centrum, B—3610, Diepenbeek, Belgium, pp. 1–15.
Strander et al., Am. Soc. for Microb., vol. 1, pp. 116–117, 1975.
De Ley et al., J. Gen. Virol., vol. 40, pp. 455–458, 1978.
Gresser, I., Proc. Soc. Exp. Biol. & Med., vol. 108, pp. 799–803, 1961.
Catalogue on Liquid Tissue Culture Media, Grand Island Biol. Co., 3175 Staley Road, Grand Island, N.Y., 10472, pp. 14, 16, 18 et seq.

*Primary Examiner*—Blondel Hazel
*Attorney, Agent, or Firm*—Vincent P. Pirri; John F. Witherspoon

[57] ABSTRACT

Pharmaceutical compositions comprising a natural mixture of Type I and Type II interferons which are produced by induction with measles vaccine virus in leukocyte cells obtained from human donors immune to measles, and methods for the preparation of such pharmaceutical compositions.

3 Claims, No Drawings

NATURAL MIXTURE OF TYPE I AND TYPE II INTERFERONS

BACKGROUND OF THE INVENTION

Interferon is a glycoprotein produced by the cells in response to viruses and some other agents named interferon inducers. Interferon possess antiviral and antitumor potential. It is presently used in clinical trials (#1).

There are two generally recognized classifications of interferon, i.e., according to the character of cells in which they are induced and according to the character of their inducer. In the former classification, fibroblast cells yield fibroblast interferon; leukocyte cells yield leukocyte interferon; and lymphoblastoid cells yield lymphoblastoid interferon. In the latter classification, any interferon induced by viruses or their nucleic acids or by synthetic inducers which in fact imitate the action of viral nucleic acids, e.g., synthetic analogue of double stranded RNA such as poly I:C, are named Type I interferon or viral interferon (independently of their producing cells). In addition to the foregoing, leukocytes were shown to produce another interferon named Type II interferon or immune interferon. Type II interferon is produced by sensitized leukocytes (from an immune animal including human) when induced by an antigen to which these leukocytes are sensitive. Non-sensitized leukocytes also produce Type II interferon when induced by certain non-viral agents such as various lectins, e.g., phytohemagglutinin (PHA) or Concanavallin A (CoA), or certain bacterial products, e.g., staphylococcal endotoxin A (SEA) (#2 and #3).

In summary, human leukocyte cells are capable of producing Type I interferon or Type II interferon. It appears that different kinds of lymphocytes are involved in the production of these Type I and Type II interferons. The Type I interferon is produced mainly by B cells whereas the Type II interferon is produced mainly by T cells. The Type I and Type II interferons differ in antigenicity. There is also a difference in their sensitivity to certain treatments. Type I interferon is stable over a wide acidic pH range (as low as about 2). On the other hand, Type II interferon is relatively pH unstable and is destroyed at a pH below about 4. The main feature which characterizes the Type I and the Type II interferons from practical point of view is that the Type II interferon was shown to possess considerably greater (up to 10 times) antitumor potential than is the case with the Type I interferon (#1). Of these two types of human leukocyte interferon only Type I (induced by Sendai virus) is presently used in clinical trails. The application of the highly active Type II interferon for clinical practice would offer obvious advantages.

Measles vaccine virus has been shown to be an effective interferon inducer of lymphoblastoid interferon (#4). The author focused on the ability of measles vaccine virus to multiply and to cause a persistent infection of the lymphoblastoid cells which are tumor-origin cells (#5). This permitted the elaboration of a model for the continuous production of lymphoblastoid interferon (#6). However, interferon induced by measles vaccine virus in lymphoblastoid cells is the usual Type I or viral interferon which does not differ from the Type I induced by the Sendai virus. Ion Gresser inoculated various leukocyte suspensions with Sendai virus, measles virus (Edmonston strain), and Polio I virus. The author reports that "after inoculation of the suspensions with either Sendai or measles virus, interferon in varying titers was detected in 21 of 22 preparations". Comparative high titer of at least 3072 is reported when Sendai virus is used as the virus. Low to essentially no titers are obtained using measles virus, namely (a) normal patient: titer at least 96 (to a maximum of 192); (b) congenital agammaglobulinemia patient: titer of 12. Leukocytes from two patients with measles rash in the absence of an added viral inducer gave no interferon titer after 3 and 7 days (#7).

One can conclude from Ion Gresser's experiments that measles virus possessed some interferon-inducing capacity, much inferior to the interferon-inducing capacity of Sendai virus. This fact apparently has not been lost sight of by subsequent researchers in the field in view of the fact that there apparently is a void in the state of the art with respect to further research on measles virus to induce interferon in leukocyte cells. On the other hand, a large body of interferon literature does indeed exist with respect to Sendai virus as an interferon inducer. Gresser did not disclose or appreciate the necessity of choosing measles sensitized leukocytes derived from a measle immune donor as the interferon-producing "factory" for the measles vaccine virus inducer. Gresser's disclosure reveals a lack of knowledge and/or appreciation that a natural mixture of Type I and Type II interferons can be induced from an in vitro medium comprising such measles sensitized leukocytes. It is not surprising, therefore, that Examples 2 and 12 of Table I of Gresser's article (#7, page 801) gave very low or relatively low interferon titers. Moreover, Examples 18 and 19 of Table I establish that presently sick, measles-infected donors (two) after 3 and 7 days did not produce interferon in vivo.

THE INVENTION

It has now been discovered quite unexpectedly and unobviously, indeed, a novel method for the production of a novel natural mixture comprising active Type I and Type II interferons which method involves the use of measles vaccine virus as the inducer of such interferons in normal immune leukocyte cells, i.e., cells obtained from human donors immune to measles.

By the term "natural mixture" comprising Type I and Type II interferons as used herein is meant a mixture of such interferons resulting from the practice of the novel method and is not to connote that such mixture was obtained by the physical addition of Type I interferon to Type II interferon or vice versa. However, the term "natural mixture" is not meant to exclude the incorporation of additional amounts of interferon(s) thereto.

By the term "normal immune leukocytes" as used herein is meant leukocyte cells from a human donor previously immunized against measles virus as a result of natural infection or immunization with measles vaccine. Thus, "normal immune leukocytes" are not cells which are tumor origin such as the various lymphoblastoid cell strains, e.g., one such line being Namalva. Conventional tests can be made with respect to the donor's blood to ascertain whether it possesses antibodies against measles virus.

In the practice of the invention normal immune leukocytes, first purified by conventional techniques well known to the art, are induced in vitro by measles vaccine virus, e.g., Edmonston's strain or Toyoshima's strain. Purification may involve, for example, utilization of Kari Cantell's process to obtain "buffy coats", followed by suspending the buffy coats in a cold solution of ammonium chloride to lyze erythrocytes, and thereafter centrifuging the resulting suspension (desirably the suspension and centrifugation steps are repeated one or more times), and recovering the sediment which contains the purified normal immune leukocytes. The sediment is then suspended in a physiological medium, e.g., a culture or maintenance medium such as MEM, Basal Medium Eagle, Medium 199 with Earles' Unmodified Salts, RPMI Medium 1629, 1634 or 1640 and the like (#8). The medium can also be an isotonic salt solution. The physiological medium may also contain other components such as a homologous protein component, e.g., up to about 5% or more of a-gamma human serum. Desirably, there is included in the medium an antibiotic(s), preferably neomycin. The pH is approximately neutral, e.g., 7 to 7.4; temperature is maintained moderately above normal room temperature, e.g., about 30° to 37° C., desirably 33° to 37.5° C.

An amount of measles vaccine virus sufficient to effect the in vitro induction of a natural mixture of active Type I and Type II interferons in the purified normal immune leukocytes is employed in accordance with techniques presently known to the art. By way of illustration one can employ $10^2$ to $10^7$, preferably $10^5$ to $10^7$, cytopathogenic doses of measles vaccine virus per ml of suspension of normal immune leukocytes. One ml of suspension can contain, for example, $10^6$ to $10^7$ leukocyte cells. The resulting suspension containing measles vaccine virus is incubated, desirably under constant stirring, for a period ranging up to several days, e.g., several hours to one week and longer. The suspension is then separated into its liquid (supernatant) and solid (sediment) fractions as by centrifugation. The solid fraction (sediment which contain leukocyte cells) can be discarded or reused. The liquid fraction (supernatant) is a crude mixture of active Type I and Type II interferons. The quantity of Type II interferon will vary, to a degree, depending on the concentration of the measles vaccine virus employed, the "degree of immunization" of the normal immune leukocytes, etc. The Type II interferon contained in the novel mixture can vary from significant minor quantities upwards to 50 percent and higher of Type II interferon in the novel mixture containing the same, e.g., 10 to 70 percent by weight and higher of Type II. The crude mixture of interferons can be subjected to conventional purification and concentration techniques to achieve the degree of purity and interferon activity desired and can be applied in the administration for prophylaxis or treatment of interferon-sensitive diseases in humans and warm blooded animals.

Desirably, the measles vaccine virus in the liquid fraction (supernatant) is inactivated according to known techniques such as by pH adjustment, e.g., lowering the pH to about 4 to 6. After this, the pH of the supernatant can be readjusted to a physiological pH, and desirably maintained at low temperature, e.g., about 0° C., until ready for use as described in my copending U.S. application Ser. No. 159,540, filed June 16, 1980, entitled "Prophylaxis or Treatment of Interferon-Sensitive Diseases", all the disclosure of which is hereby incorporated by reference. Alternatively, the supernatant can be further processed as by conventional purification and/or concentration techniques and thereafter used in the administration for prophylaxis or treatment of interferon-sensitive diseases.

The liquid mixture containing Type I and Type II interferons can be converted to a solid form, e.g., tablet, rod, pellet, capsule, etc., especially by lyophilization, thereafter containerized, stored, and when ready for use it can be dissolved in measured quantities of a diluent, e.g., water, to which medicaments and other additives can be incorporated, e.g., glycerol, low molecular weight polyethylene glycol, buffering agents, fragrances, stabilizers, antibiotics, nutrients, transfer factor, thyrosin, vitamins, trace elements, glucose, etc. The resulting pharmaceutical preparation can be used in the administration for prophylaxis or treatment of interferon-sensitive diseases as indicated previously.

In the practice of the invention there is achieved a high degree of efficiency which heretofore has not been realized. The novel method utilizes both the lymphocyte B and T cells, the main cells for the production of interferon, in a non-tumor origin environment, to yield an active natural mixture comprising Type I and II interferons, a "superinterferon" so to speak. Additionally, the measles vaccine virus inducer is relatively non-toxic when compared with, for example, staphylococcal endotoxin A (SEA) inducer which is reputed to induce only Type II interferon. More significantly, however, the measle vaccine virus is easily inactivated in the novel natural mixture of Type I and Type II interferons by mere pH adjustment. Prior art interferon production methods, on the other hand, do not appear to have achieved total utilization of the lymphocyte cells in interferon induction since such methods utilize either the lymphocyte B cells to produce Type I interferon (by viral induction) or the lymphocyte T cells to produce Type II interferon (by antigen induction).

The following Examples are illustrative.

EXAMPLE 1

Measles vaccine virus (e.g., Edmonston's strain or Toyoshima strain) is propagated in the embryonated chicken eggs. The virus ($10^2$ cytopathogenic doses per 0.2 ml) is injected by a syringe in the chorion-allantoic cavity of twelve-day old chicken embryos. After 40 hours to 48 hours incubation at about 34° C., the amniotic and allantoic fluids are harvested and used as the virus. Five percent human a-gamma serum is added in order to increase the virus stability. Virus is kept at $-70°$ C. in a liquid or lyophilized form. The resulting titer generally does not exceed $10^5$ cytopathogenic doses/ml and may be concentrated by conventional techniques, e.g., to about $10^7$ cytopathogenic doses per ml by ultracentrifugation.

EXAMPLE 2

A. Normal leukocytes are suspended ($10^7$ cell/ml) in the RPMI Medium 1640 supplemented wit 2% of human a-gamma serum and neomycin (25 micrograms/ml). This suspension is inoculated with measles virus ($10^2$ cytopathogenic doses/ml) and incubated under constant stirring (40 revolutions/minute) at a temperature of 33.5° C. After 36 to 48 hours, the suspension is centrifuged (3000 rpm, 5 min. at 0° C.). The sediment (cells) are resuspended in a small volume (1/20 to 1/10 of the volume of original suspension) of hypotonic buffer solution and the cells are destroyed by repeated freeze-defreezing cycles (2-3 times). This procedure allows the leaking of intracellular virus into the solution. After centrifugation (3000 rpm, 5 min., at 0° C.), the pellet formed by cellular debris is discarded. Supernatant (II) containing measles virus derived from disrupted cells is added to the supernatant (I). The resulting liquid (ph 7.4) supplemented with 5% human a-gamma serum serves as the virus, and is kept at −70° C. in a liquid or lyophilized form (preferred). The resulting titer generally does not exceed $10^7$ cytopathogenic doses/ml.

B. The same virus as above can be propagated using, as the tissue cultures therefor, human diploid fibroblasts, human amnion, and others.

EXAMPLE 3

Buffy coats of leukocytes non-immune to measles, obtained by centrifugation of the whole blood, are suspended in cold 0.83% aqueous solution of $NH_4Cl$. After 10 minutes incubation at 4° C., the suspension is centrifuged (approximately 1500 rpm, about 5 minutes, 0° C.). This procedure is repeated again thus destroying the erythrocytes. After a second treatment with cold 0.83% aqueous solution of ammonium chloride, the purified leukocytes are resuspended in the culture medium, i.e., Minimal Essential Medium (MEM) with 4% a-gamma human serum and neomycin (25 micrograms/ml). The suspension of leukocytes ($10^6$ to $10^7$ cell/ml) is inoculated with measles vaccine virus ($10^5$ to $10^7$ cytopathogenic doses/ml) of Example 1.

The resulting inoculated suspension is incubated at about 37° C. under an air-$CO_2$ (10%) blanket with stirring (40 revolutions/minute). Interferon is harvested after 30–36 hours of incubation. The suspension is centrifuged (approximately 3000 rpm, about 10 minutes, 0° C.). The supernatant contains Type I interferon of a relatively low titer (antiviral effect on vesicula stomatitis virus (VSV); about 10 to $10^2$ units/ml), no Type II interferon, and live measles vaccine virus. The measles vaccine virus can be inactivated by lowering the pH of the supernatant to a value of about 5 to 6. Further processing of the Type I interferon is not deemed to be worthwhile in view of its low titer. Sendai virus inducer, on the other hand, under the conditions noted above provides a hundred fold increase, and more, of Type I interferon.

EXAMPLE 4

The procedure of Example 3 is repeated except that the measles virus of Example 2A is employed as the interferon inducer. There is obtained a supernatant containing Type I interferon exhibiting a relatively low titer, i.e., approximately 10 to $10^2$ units/ml. No Type II interferon was detected in the supernatant.

On the other hand, Sendai virus is easily propagated in chicken embryos yielding concentrations up to $10^9$ cytopathogenic doses/ml. A special strain of Sendai virus isolated by Dr. Kari Cantell exhibits high potency as an interferon inducer, e.g., titer of about $10^3$ to $5 \times 10^4$ units/ml, and more, of Type I interferon.

EXAMPLE 5

The procedure of Example 3 is repeated except that normal immune leukocytes (those obtained from human donors who are immune to measles) and the measles virus of Example 1 are employed. There is obtained a supernatant containing a crude mixture of Type I and Type II interferons. The titer of Type I interferon in this mixture is about $10^3$ to $3 \times 10^4$ units/ml. The titer of Type II interferon is about $10^2$ to $10^4$ units/ml.

EXAMPLE 6

The procedure of Example 3 is repeated except that there are employed the normal immune leukocytes (those obtained from human donors who are immune to measles) and the measles virus of Example 2. There is obtained a supernatant containing a crude mixture of Type I and Type II interferons. The titer of each type (I and II) reaches about $10^4$ unit/ml, and even higher.

Inasmuch as Type II interferon is reported to possess at least ten times, and higher, antitumor potential than Type I interferon, the crude natural mixture of Type I and Type II interferons which is obtained by the practice of the invention can be aptly termed "natural superinterferon". Furthermore, this crude natural mixture also contains live measles vaccine virus which, fortunately, is pH sensitive in the acidic range and is readily inactivated at a pH of 6 and lower. Type II interferon is stable at an acidic pH above about 3.5 whereas Type I interferon is stable at a still lower acidic pH, i.e., pH of 2 and higher. Therefore, the pH of the supernatant is lowered to about 4.5 to inactivate the measles virus vaccine. After virus inactivation the pH of the resulting crude mixture of active Type I and Type II interferons is adjusted to 7.2. This mixture of crude interferons containing a substantial minor quantity of Type II interferon can be subjected to conventional purification and concentration techniques such as precipitation, evaporation, centrifugation, chromatography, adsorption, lyophilization, and the like. The crude or purified mixture of interferons (I and II) can be used in the administration for prophylaxis or treatment of interferon-sensitive diseases in humans and other warm blooded mammals.

A unit of interferon, as used herein, is the reciprocal of the dilution of an interferon preparation which causes 50% protection against cytopathogenic effect of vesicular stomatitis in tissue culture. An adjustment is made against an international standard preparation 69/15 (#9).

LIST OF CITATIONS

1. Yabrov, A., textbook entitled *Interferon and Nonspecific Resistance*, Human Sciences Press, New York, N.Y. (1980).
2. Epstein, L., "The Comparative Biology of Immune and Classical Interferons," in *Biology of the Lymphokines*, Academic Press, Inc., New York, N.Y., 1979, pages 445–447, 453–454.
3. Osborne, L. et al., "Classification of Interferons with Antibody to Immune Interferon," *Cellular Immunology*, Vol. 53, pages 65–70 (1980).
4. Volckaert-Vervliet, G. et al., "Induction of Interferon in Human Lymphoblastoid Cells by Sendai and Measles Viruses," Department of Chemistry, Biology & Microbiology, Limburgs Universitair Centrum, B—3610 Diepenbeek, Belgium, pages 1–15.
5. Strander, H. et al., "Production of Human Lymphoblastoid Interferon," *American Society for Microbiology*, Vol. 1, No. 1, pages 116–117 (1975).
6. De Ley, M. et al., "A Semi-Continuous System for the Production of Human Interferon in Lymphoblastoid Cell Cultures," *J. General Virology*, Vol. 40, pages 455–458 (1978).
7. Gresser, I., "Production of Interferon by Suspensions of Human Leukocytes," *Proc. Soc. Exp. Biol. & Med.*, Vol. 108, pages 799–803 (1961).

8. Catalogue on Tissue Culture Products, Grand Island Biological Company (GIBCO), 3175 Staley Road, Grand Island, N.Y. 10472, pages 14, 16, 18 et seq.
9. Miscellaneous—*Interferons;* Research Reference Reagents Note #16A; "Freeze-dried Human Fibroblast Reference Interferon (G023-902-527)."

What is claimed is:

1. A method of producing in vitro a natural mixture of Type I and Type II interferons which comprises adding measles vaccine virus to a physiological medium containing normal immune leukocyte cells obtained from human donors immune to measles; incubating the resulting admixture for a period of time sufficient to induce a natural mixture of Type I and Type II interferons in the cells contained in said medium; and recovering a suspension containing said natural mixture of Type I and Type II interferons.

2. The method of claim 1 wherein said suspension is separated into a liquid fraction containing the natural mixture of Type I and Type II interferons and measles vaccine virus and a solid fraction containing said normal immune leukocyte cells.

3. The method of claim 2 wherein the measles vaccine virus in the liquid fraction is inactivated.

* * * * *